United States Patent
Schalau, II et al.

US007914645B2

(10) Patent No.: US 7,914,645 B2
(45) Date of Patent: Mar. 29, 2011

(54) SILICONE ADHESIVE FOR ADHESION TO WET SURFACES

(75) Inventors: Gerald Kenneth Schalau, II, Freeland, MI (US); Xavier Jean-Paul Thomas, Rhode-Saint-Genese (BE); Victor Albert Raul, Midland, MI (US); David Clayton Gantner, Midland, MI (US); Katherine Lynn Ulman, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 268 days.

(21) Appl. No.: 12/158,718

(22) PCT Filed: Jan. 3, 2007

(86) PCT No.: PCT/US2007/000062
§ 371 (c)(1),
(2), (4) Date: Jun. 23, 2008

(87) PCT Pub. No.: WO2007/084266
PCT Pub. Date: Jul. 26, 2007

(65) Prior Publication Data
US 2008/0295960 A1    Dec. 4, 2008

Related U.S. Application Data

(60) Provisional application No. 60/760,254, filed on Jan. 19, 2006.

(51) Int. Cl.
C09J 7/02        (2006.01)
A61F 13/02      (2006.01)
C08F 283/00    (2006.01)

(52) U.S. Cl. ................... 156/329; 424/448; 525/477

(58) Field of Classification Search ............. 156/329; 424/448; 523/109, 120
See application file for complete search history.

(56) References Cited

U.S. PATENT DOCUMENTS

| | | | |
|---|---|---|---|
| 2,736,721 A | 2/1956 | Dexter | |
| 2,814,601 A | 11/1957 | Currie et al. | |
| 2,857,356 A | 10/1958 | Goodwin | |
| 3,402,192 A | 9/1968 | Haluska | |
| 3,641,239 A | 2/1972 | Mohrlok | |
| 3,742,951 A | 7/1973 | Zaffaroni | |
| 3,836,647 A * | 9/1974 | Lange | 514/63 |
| 4,584,355 A | 4/1986 | Blizzard et al. | |
| 4,585,836 A | 4/1986 | Homan et al. | |
| 4,591,622 A | 5/1986 | Blizzard et al. | |
| 4,591,652 A | 5/1986 | DePasquale et al. | |
| 4,655,767 A | 4/1987 | Woodard et al. | |
| 5,098,299 A | 3/1992 | Fischer | |
| 5,136,068 A | 8/1992 | Bahr et al. | |
| 5,145,933 A | 9/1992 | Grisoni et al. | |
| 5,154,849 A * | 10/1992 | Visscher et al. | 510/150 |
| 5,175,058 A * | 12/1992 | Traver | 428/447 |
| 5,248,739 A * | 9/1993 | Schmidt et al. | 525/477 |
| 5,380,527 A | 1/1995 | Legrow et al. | |
| 5,482,988 A | 1/1996 | Ulman et al. | |
| 5,488,124 A | 1/1996 | Cobb et al. | |
| 5,496,544 A * | 3/1996 | Mellul et al. | 424/78.03 |
| 5,561,203 A * | 10/1996 | Strong et al. | 525/477 |
| 5,602,214 A * | 2/1997 | Lin et al. | 525/478 |
| RE35,474 E | 3/1997 | Woodard et al. | |
| 5,612,400 A * | 3/1997 | Gross et al. | 524/268 |
| 5,623,017 A | 4/1997 | Hill | |
| 5,658,975 A | 8/1997 | Ulman et al. | |
| 5,700,478 A * | 12/1997 | Biegajski et al. | 424/434 |
| 5,707,550 A | 1/1998 | Glover et al. | |
| 5,811,487 A | 9/1998 | Schulz, Jr. et al. | |
| 5,831,080 A | 11/1998 | Sejpka et al. | |
| 5,869,556 A * | 2/1999 | Cifuentes et al. | 524/394 |
| 6,121,373 A | 9/2000 | Starch | |
| 6,133,370 A | 10/2000 | Gutek et al. | |
| 6,319,510 B1 | 11/2001 | Yates | |
| 6,325,993 B1 | 12/2001 | Saito et al. | |
| 6,406,683 B1 * | 6/2002 | Drechsler et al. | 424/64 |
| 6,517,933 B1 | 2/2003 | Soane et al. | |
| 6,569,408 B1 * | 5/2003 | Yue et al. | 424/49 |
| 6,669,930 B1 * | 12/2003 | Hoic et al. | 424/49 |
| 6,685,921 B2 * | 2/2004 | Lawlor | 424/49 |
| 6,692,727 B1 * | 2/2004 | Yue et al. | 424/53 |
| 6,967,024 B2 * | 11/2005 | Scancarella et al. | 424/401 |
| 7,199,205 B2 | 4/2007 | Okawa et al. | |

(Continued)

FOREIGN PATENT DOCUMENTS

| | | |
|---|---|---|
| EP | 0180377 | 1/1991 |
| WO | WO03/50144 | 6/2003 |
| WO | WO2005/092300 | 10/2005 |

(Continued)

*Primary Examiner* — Randy Gulakowski
*Assistant Examiner* — Robert Loewe
(74) *Attorney, Agent, or Firm* — Sharon K. Brady

(57) ABSTRACT

A silicone adhesive composition used for adhering a device or a substance to a wet surface contains (i) a silicone resin that is cohydrolysis product of a trialkyl hydrolyzable silane and an alkyl silicate in which the cohydrolysis product contains a plurality of silicon-bonded hydroxy groups; (ii) a linear organopolysiloxane fluid containing terminal silicon-bonded hydroxy groups having a viscosity above 200,000 mm$^2$/$_s$ at 25° C.; (iii) a trialkylsiloxy terminated polyorganosiloxane fluid having a viscosity of 100,000-600,000 mm$^2$/$_s$ at 25° C.; (iv) a water soluble muco-adhesive polymer selected from the group consisting of a poly(ethylene oxide) polymer having a molecular weight of 100,000 to 8,000,000, an acrylic acid polymer having a molecular weight of 500,000 to 4,500,000,000, and a hydroxyethylcellulose polymer having a molecular weight of 90,000 to 1,300,000,000; and optionally, (v) a solvent selected from the group consisting of aliphatic hydrocarbons, aromatic hydrocarbons, esters, volatile linear and cyclic silicone compounds. Other components such as a silicone polyether, a silicone wax, a drug, an excipient, and/or an active ingredient can also be included.

4 Claims, No Drawings

U.S. PATENT DOCUMENTS

| | | |
|---|---|---|
| 2003/0044599 A1 | 3/2003 | Sugii et al. |
| 2003/0065086 A1* | 4/2003 | Kosal ............................ 524/588 |
| 2004/0141933 A1* | 7/2004 | Luo et al. ........................ 424/64 |
| 2004/0166068 A1* | 8/2004 | Rajaiah et al. .................. 424/49 |
| 2005/0089498 A1* | 4/2005 | Patil et al. ................ 424/70.122 |
| 2005/0118124 A1* | 6/2005 | Reinhart et al. ................ 424/63 |
| 2005/0228066 A1* | 10/2005 | Wong et al. .................... 523/120 |
| 2006/0128921 A1* | 6/2006 | Cray et al. ...................... 528/31 |

* cited by examiner

SILICONE ADHESIVE FOR ADHESION TO WET SURFACES

CROSS REFERENCE TO RELATED APPLICATIONS

This application is a U.S. national stage filing under 35 U.S.C. §371 of PCT Application No. PCT/US07/000,062 filed on 3 Jan. 2007, currently pending, which claims the benefit of U.S. Provisional Patent Application No. 60/760,254 filed 19 Jan. 2006 under 35 U.S.C. §119 (e). PCT Application No. PCT/US07/000,062 and U.S. Provisional Patent Application No. 60/760,254 are hereby incorporated by reference.

FIELD OF THE INVENTION

This invention relates to a silicone adhesive composition that has enhanced adhesion to wet biological surfaces including the gums, the buccal cavity, mucosal linings, and wet surface skin. The silicone adhesive composition can be used to adhere medical devices such as topical patches and transdermal patches, or other drug delivery devices, dentures, hairpieces, ostomies, tapes, and wound dressings, to wet surfaces. The silicone adhesive composition is compatible with many drugs and/or active ingredients; effectively releases drugs from matrices containing the silicone adhesive composition, drug, and/or active ingredient; and provides effective adhesion to skin that is submerged in water. The silicone adhesive composition may be used in the form of a paste, bead, patch, or extruded device.

BACKGROUND OF THE INVENTION

Silicone adhesive compositions can be pressure sensitive or permanent bonding types of adhesives. Permanent bonding implies that the adhesive will actually cement two surfaces together, i.e., it behaves like a glue. Pressure sensitive, on the other hand, means that the adhesive can be stripped from a surface and re-adhered to the surface, i.e., it has the nature of the adhesive present on Scotch® Brand tapes. The adhesive of the invention are pressure sensitive adhesives but can be formed into permanent bonding adhesives when combined with a suitable crosslinking agent such as a hydrogen bearing silicone polymer, and a catalyst.

Typically, the components of a silicone pressure sensitive adhesive consist of (i) a silicone resin containing monofunctional (M) units $R_3SiO_{1/2}$ and tetrafunctional (Q) units $SiO_4$, i.e., an MQ silicone resin, wherein R is a hydrocarbon group such as methyl; and (ii) a high molecular weight hydroxyl endblocked polydiorganosiloxane fluid with a viscosity of 5,000 to 1,000,000 $mm^2/s$ at 25° C., or a high molecular weight hydroxyl endblocked polydiorganosiloxane gum where viscosity is expressed in terms of plasticity.

Silicone pressure sensitive adhesives can be prepared by simply mixing components (i) and (ii). Generally, this takes place in the presence of a mutual solvent such an organic, aromatic or a hydrocarbon solvent, i.e., ethyl acetate, heptane, xylene, or toluene. However, the solvent can be omitted. As soon as components (i) and (ii) mixed, the composition is ready for use as a pressure sensitive adhesive without further treatment. It can simply be applied to the surfaces to be adhered by any suitable means, and then the surfaces are brought together. Typically, if the composition contains a solvent, the solvent is allowed to evaporate before adhering the two surfaces. The coating can be cured for a short time by heating it briefly, although curing is not generally required. Likewise, a catalyst can be added to assist in the curing, although a catalyst is not generally required.

Silicone pressure sensitive adhesives are described in U.S. Pat. No. 2,736,721 (Feb. 28, 1956); U.S. Pat. No. 2,814,601 (Nov. 26, 1957); U.S. Pat. No. 2,857,356 (Oct. 21, 1958); U.S. Pat. No. 4,584,355 (Apr. 22, 1986); U.S. Pat. No. 4,585,836 (Apr. 29, 1986); U.S. Pat. No. 4,591,622 (May 27, 1986); U.S. Pat. No. 4,655,767 (Apr. 7, 1987): and U.S. Pat. No. 5,482,988 (Jan. 9, 1996). In addition, other types of adhesives having a more suitable surface pressure sensitive adhesion property can be used, such as the so-called Soft Skin Adhesive, i.e., the siloxane gel compositions described in detail in U.S. Pat. No. 5,145,933 (Sep. 8, 1992), which are prepared from (A) alkenyl-containing polydiorganosiloxanes, (B) hydrosilicon compounds having at least three SiH groups, (C) SiH end-blocked polydiorganosiloxanes, and a (D) catalyst. None of these patents, however, either describe or suggest the silicone pressure sensitive adhesive compositions according to the invention that are capable of adhering to wet surfaces.

BRIEF SUMMARY OF THE INVENTION

The invention is directed to a silicone adhesive composition and to a method of adhering a device or a substance to a wet surface by applying a silicone adhesive composition to the wet surface. The silicone adhesive composition contains:
(i) a silicone resin that is a cohydrolysis product of a trialkyl hydrolyzable silane and an alkyl silicate in which the cohydrolysis product contains a plurality of silicon-bonded hydroxy groups;
(ii) a linear organopolysiloxane fluid containing terminal silicon-bonded hydroxy groups having a viscosity above 200,000 $mm^2/s$ at 25° C.;
(iii) a trialkylsiloxy terminated polyorganosiloxane fluid having a viscosity of 100,000-600,000 $mm^2/s$ at 25° C.;
(iv) a water soluble muco-adhesive polymer selected from the group consisting of a poly(ethylene oxide) polymer having a molecular weight of 100,000 to 8,000,000, an acrylic acid polymer having a molecular weight of 500,000 to 4,500,000,000, and a hydroxyethylcellulose polymer having a molecular weight of 90,000 to 1,300,000,000; and optionally,
(v) a solvent selected from the group consisting of aliphatic hydrocarbons, aromatic hydrocarbons, esters, volatile linear and cyclic silicone compounds.

The silicone adhesive composition may include other components such as a silicone polyether, a silicone wax, a drug, an excipient, and/or an active ingredient. It is useful for attaching to wet surfaces devices such as a denture, a hairpiece, a prosthesis, an ostomy, a wound dressing, a tape, a buccal patch, or a transdermal patch. Devices and substances can also be attached to wet surfaces such as skin, the buccal cavity, the gums, the mucosal linings of intranasal passages, the alimentary canal, vaginal and rectal walls, and wet components of botanical origin. These and other features of the invention will become apparent from a consideration of the detailed description.

DETAILED DESCRIPTION OF THE INVENTION

Generally, the silicone adhesive composition of the invention includes a silicone resin, a linear organopolysiloxane fluid containing silicon-bonded hydroxy groups, a polydimethylsiloxane fluid, and a water soluble muco-adhesive polymer selected from the group consisting of a poly(ethylene oxide) polymers, acrylic acid polymers, and hydroxyethylcellulose polymers. Enhanced adhesion to wet surfaces provided by adhesive compositions of the invention is obtained by the presence in the composition of the water soluble muco-adhesive polymer component. These and other essential and optional components of the silicone adhesive composition are described below.

The Silicone Resin/Linear Organopolysiloxane Fluid

The silicone adhesive composition contains (i) a silicone resin and (ii) a linear organopolysiloxane fluid. The silicone resin is a reaction product obtained as a result of cohydrolyzing a trialkyl hydrolyzable silane and an alkyl silicate. The resulting cohydrolysis product contains a plurality of silicon-bonded hydroxy groups. The linear organopolysiloxane fluid is a high viscosity organopolysiloxane fluid containing terminal silicon-bonded hydroxy groups. The viscosity of the linear organopolysiloxane fluid containing terminal silicon-bonded hydroxy groups is above 200,000 mm$^2$/s at 25° C. or alternatively is from 200,000 mm$^2$/s to 3,000,000 mm$^2$/s at 25° C. The cohydrolysis product and the linear organopolysiloxane fluid can be intercondensed by combining one part by weight of the cohydrolysis product and 0.5-6 parts by weight of the linear organopolysiloxane fluid. These components and the methods of preparing the components are described in detail in U.S. Pat. No. 2,857,356 (Oct. 21, 1958).

The Trialkylsiloxy Terminated Polydiorganosiloxane Fluid

The trialkylsiloxy terminated polydiorganosiloxane fluid (iii), preferably a trimethylsiloxy terminated polydimethylsiloxane fluid, has a viscosity of 100,000-600,000 mm$^2$/s at 25° C. The fluid may contain all alkyl groups, or it may contain alkyl groups and aryl groups. These polydiorganosiloxane fluids generally have a weight average (Mw) molecular weight of from about 130,000-260,000. The polydiorganosiloxane fluid may be a polymer or copolymer, and may have a straight-chain or a branched chain provided the viscosity is within the desired range. Generally, the polydiorganosiloxane fluid will have a structure corresponding to the formulae shown below, wherein m and n represent integers having a value sufficient to provide the desired molecular weight; and wherein R represents the same or different alkyl groups, i.e. methyl or ethyl, and R1 represents an alkyl or aryl group, i.e., phenyl. The alkyl groups R may contain 1-8 carbon atoms such as methyl, ethyl, propyl, butyl, pentyl, hexyl, heptyl, and octyl, but R is typically methyl or ethyl.

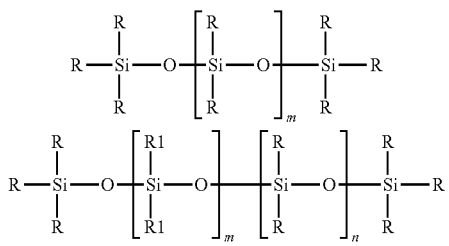

Illustrative polydiorganosiloxane fluids include polydimethylsiloxane, polydiethylsiloxane, polymethylethylsiloxane, polymethylphenylsiloxane, and polydiphenylsiloxane. These polydiorganosiloxane fluids are well known in the art, and are commercially available from chemical suppliers such as the Dow Corning Corporation, Midland, Mich.

The Water Soluble Muco-Adhesive Polymer

Component (iv) of the invention is a water soluble muco-adhesive polymer. As used herein, water soluble muco-adhesive polymer encompasses any high molecular weight polymer that adheres to wet surfaces, particularly muco surfaces, and yet is soluble in water. The water soluble muco-adhesive polymer may consist of many different functionalities, including poly(ethylene oxide) polymers (PEOP), acrylic acid based polymers, and hydroxyethylcellulose polymers. This water soluble muco-adhesive polymer is the unique component of the invention that provides the improved and enhanced adhesion to wet surfaces, and the feature distinguishing the compositions herein from the prior art.

Poly(ethylene oxide) polymers useful herein are nonionic, high molecular weight polymers. These polymers have weight average (Mw) molecular weights ranging from 100,000-8,000,000, preferably ranging from 600,000-4,000,000. Generally, poly(ethylene oxide) polymers are known to be capable of delivering many desirable properties such as binding, thickening lubricity, adhesion, thickening, and film formation. Poly(ethylene oxide) polymers conform generally to the formula H(OCH$_2$CH$_2$)nOH where n has a value sufficient to provide the desired molecular weight. Poly(ethylene oxide) polymers are available commercially under the trademark POLYOX® from The Dow Chemical Company, Midland, Mich. These polymers are most preferred for use herein.

Acrylic acid polymers are also useful herein and are high molecular weight, crosslinked, acrylic acid based polymers that may be cross-linked with allyl sugars such as allyl sucrose, or allyl sugar alcohols such as allylpentaerythritol. They may also be modified by long chain C$_{10}$-C$_{30}$ alkyl acrylates and crosslinked with allylpentaerythritol. Typical molecular weights of these polymers range from 500,000 to 4,500,000,000. Acrylic acid polymers are available commercially under the trademark CARBOPOL® from Noveon Incorporated, Cleveland, Ohio.

Hydroxethylcellulose polymers are another type of polymer useful herein and they are non-ionic water soluble polymers derived from cellulose, that may be polymerized to varying degrees to provide different solubilization parameters. The molecular weights of these polymers range from 90,000 to 1,300,000,000. Hydroxyethylcellulose polymers are available commercially from Hercules Incorporated, Wilmington, Del.

Optional Components

The silicone adhesive may contain other optional components designed to enhance one or more of the physical properties or tack of the final silicone adhesive product. Among the optional components that can be used in the silicone adhesive are a solvent, a silicone polyether, a silicone wax, and various drugs.

The Solvent

The silicone adhesive can include a solvent component (vi) to provide a solvated silicone adhesive in which case the silicone resin and the silicone fluid are added to a solvent solution. The solvent is preferably a volatile solvent that can be evaporated from the solvated silicone adhesive solution by ambient air, forced drafts, or heated ovens. It has been determined that the resulting silicone adhesive will effectively adhere to wet surfaces such as human skin even while the skin is submerged in cool water. Some examples of suitable volatile organic solvents are aliphatic hydrocarbons such as heptane, isododecane, and hexane; volatile aromatic hydrocarbons such as toluene, benzene, and xylene; and volatile esters such as ethyl acetate. Low molecular weight linear and cyclic silicone compounds can also be used such as hexamethyldisiloxane, octamethyltrisiloxane, decamethyltetrasiloxane, octamethylcylotetrasiloxane, decamethylcyclopentasiloxane, and dodecamethylcyclohexasiloxane. The use of a solvent is optional, however, and the solvent can be omitted in those instances where solventless silicone pressure sensitive adhesives are desired. This is common practice, for example, in the customization of solventless silicone pressure sensitive adhesives having adjustable tack.

The Silicone Polyether

A silicone polyether (vi) can be included in the silicone adhesive whenever it is desired to adjust the release profile of a drug. Silicone polyethers which can be used in the method of this invention are preferably copolymeric silicone polyethers containing dimethylsiloxy units and oxyalkylene units in their molecule. These silicone polyethers have a structure generally corresponding to the formula:

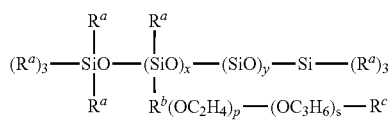

In the formula, $R^a$ is an alkyl group of one to six carbon atoms; $R^b$ is the radical $—C_mH_{2m}—$; $R^c$ is a terminating radical including a hydroxyl group, an alkoxy group, or an acetoxy group; m has a value of 2-8; p and s have values such that the oxyalkylene segment $—(OC_2H_4)_p—(OC_3H_6)_s—$ has a molecular weight in the range of 400 to 5,000; the segment preferably having 50-99 mole percent of oxyethylene units $—(OC_2H_4)_p—$, and 1-50 mole percent of oxypropylene units $—(OC_3H_6)_s—$; x has a value of 80-400; and y has a value of 2-10. Silicone polyethers containing only one oxyalkylene segment can also be used.

Such silicone polyethers are well know in the art, commercially available, and described in detail in detail in U.S. Pat. No. 3,402,192 (Sep. 17, 1968), and more recently in, for example, U.S. Pat. No. 6,121,373 (Sep. 19, 2000). If desired, other types of silicone polyethers can be used, but it may result in failure to obtain all of benefits of the invention.

Thus, some representative examples of other types of silicone polyethers which may be considered can be found described in detail in the following patents, (i) crosslinked silicone polyethers in U.S. Pat. No. 5,136,068 (Aug. 4, 1992); (ii) waxy silicone polyethers in U.S. Pat. No. 5,482,988 (Jan. 9, 1996); (iii) oligomeric silicone polyethers in U.S. Pat. No. 5,488,124 (Jan. 30, 1996); (iv) short chain low molecular weight silicone polyethers and cyclic silicone polyethers in U.S. Pat. No. 5,623,017 (Apr. 22, 1997); (v) oxyalkylene functional silanes in U.S. Pat. No. 5,707,550 (Jan. 13, 1998); (vi) elastomeric silicone polyethers in U.S. Pat. No. 5,811,487 (Sep. 22, 1998); and (vii) silicone polyethers containing arylalkyl groups in U.S. Pat. No. 6,133,370 (Oct. 17, 2000); all of which are considered incorporated herein by reference thereto.

The Silicone Wax

A silicone wax (vii) can be included in the silicone adhesive whenever it is desired to adjust the tack of the final silicone adhesive product. These silicone waxes are generally alkylmethylpolysiloxanes in which there is present in the molecule at least one alkyl group containing 18-45 carbon atoms. Typically, these silicone waxes have the formula $R_3SiO(R_2SiO)_x(RR'SiO)_ySiR_3$ in which in which R denotes an alkyl group containing 1-8 carbon atoms; R' is R is $C_nH_{2n+1}$ in which n is 18-45; x is 2-200, and y is 3-40. The silicone wax should have a melting point above ambient or room temperature (20-25° C.). One preferred silicone wax is polymethylstearylsiloxane. These silicone waxes are well known in the art, and are commercially available from chemical suppliers such as the Dow Corning Corporation, Midland, Mich. Silicone waxes are described in the patent literature, for example, U.S. Pat. No. 3,641,239 (Feb. 8, 1972) and U.S. Pat. No. 5,380,527 (Jan. 10, 1995).

The Drug

A drug (viii) can be included in the silicone adhesive whenever it is desired to deliver a drug as an active ingredient to the surface to which the silicone adhesive is applied. The drug may be a hydrophilic drug or a lipophilic drug. The term drug as used herein is intended to mean substances defined as drugs under the Federal Food, Drug, and Cosmetic Act, Pub. L. No. 75-717, 52 STAT. 1040 (1938), 21 USC Sec. 201. [321]. Generally, drugs according to Sec. 201 [321] (g)(1) (B) and (C) are substances intended for use in the diagnosis, cure, mitigation, treatment, or prevention of disease in man or other animals; and substances, other than food, intended to affect the structure or any function of the of the body of man or other animal.

Some representative examples of such substances are (i) drugs that act upon the central nervous system such as clozapine, risperidone, chlordiazepoxide, buspirone, desipramine, maprotiline, amitriptyline, timolol, selegiline, naloxone and nalbuphine; (ii) drugs affecting renal and cardiovascular function such as acetazolamide, isosorbide, furosemide, chlorothiazide, amiloride, captopril, enalapril, lisinopril, isosorbide nitrate, nifedipine, verapamil, phenyloin, lidocaine, propranolol, amiodarone, pravastatin, probucol and ciprofibrate; (iii) drugs affecting gastrointestinal function such as cimetidine, omeprazole and ranitidine; (iv) drugs for the treatment of helminthiasis such as thiabendazole and mebendazole; (v) drugs for the treatment of microbial diseases such as trimethoprim, norfloxacin, ciprofloxacin, penicillin G nafcillin, cephalothin cefazolin, kanamycin A, neomycin, doxycycline minocycline, clarithromycin, clindamycin, flucytosine, ketoconazole, fluconazole, acyclovir and ganciclovir; (vi) drugs for the treatment of neoplastic diseases such as dacarbazine, busulfan, and triazenes; (vii) drugs for the treatment of nutrient deficiency such as folic acid, niacinamide, ascorbic acid and thiamine; (viii) drugs for hormonal replacement therapy such as estradiol, ethinyl estradiol and norethindrone; (ix) drugs that inhibit the synthesis and actions of adrenocortical hormones such as cortisol, cortisone and prednisone; (x) drugs used in dermatology for the treatment of dermatoses such as betamethasone dipropionate, hydrocortisone, dexamethasone sodium phosphate, retinal, tretinoin, isotretinoin, dapsone, calipotriene, ketoconazole, clotrimazole, itraconazole and arotinoid; (xi) prostaglandins (PG's) such as PGA, PGD, PGE, PGF, PGI 6-keto-PGE, 6,9-nitrilo-PGI, 6,9-methano-$PGI_2$ and derivatives thereof, (xii) vasodilatives such as nitroglycerin; (xiii) antiinflammatory agents such as indomethacin and ibuprofen; (xiv) antibiotics such as penicillin and erythromycin; (xv) hypnotic sedatives such as phenobarbital; (xvi) anesthetics such as benzocaine; (xvii) antibacterial agents such as pentamycin; (xviii) vitamins such as vitamin A; and (xix) anticonvulsants such as atropine.

An excipient can be included and is intended to mean substances as defined in the *Handbook of Pharmaceutical Excipients*, Ray. C. Rowe, Paul J. Weller, and Arthur H. Kibbe, (Editors), as additives used to convert pharmacologically active compounds into pharmaceutical dosage forms suitable for the administration to patients. Some representative examples of such additives are (i) sugars and sugar derivatives such as acacia, dextrin, dextrose, fructose, lactose, maltodextrin, mannitol, sorbitol, sucrose, and xylitol; (ii) starch derivatives; (iii) cellulosic materials such as sodium carboxymethylcellulose, microcrystalline cellulose, cellulose acetate phthalate, sodium croscarmellose, methyl cellulose, ethylcellulose, hydroxyethylcellulose, hydroxypropylcellulose, hydroxypropylmethylcellulose, and hydroxypropylmethylcellulose phthalate; (iv) polysaccharides such as dextrates, guar gum, and xanthan gum; (v) polyethers such as poloxamer and polyoxyethylene alkyl ethers; (vi) polyvinyl alcohols; (vii) acrylic and methacrylic acid polymers such as Carbopol, Carbomer, polacrilin potassium, and polymethacrylates; (viii) pyrrolidone derivatives such as povidone and crospovidone; (ix) glycuronam polymers and derivatives such as alginic acid and the calcium and sodium alignate salts thereof; (x) solid diluents such as the calcium and magnesium salts of carbonates, calcium phosphate derivatives, calcium sulfate, magnesium oxide, potassium chloride, and potassium citrate; (xi) solid lubricants such as calcium and magnesium stearate derivatives, talc, and zinc oxide; (xii) suspending agents such as kaolin, magnesium aluminum silicate, carbon, and cyclodextrins; and (xiii) others excipient substances such as cholesterol, fumaric acid, lecithin, gelatin, malic acid, sodium bicarbonate, sodium citrate salts, sodium stearyl fumarate, titanium dioxide, and zinc oxide.

Miscellaneous Optional Components

Other miscellaneous optional components (ix) commonly used in silicone adhesives can be included herein such as polyvinylpyrrolidones (PVP), sometimes referred to as polyvinylpyrrolidinones, which can function as cohesive strengthening agents. PVPs $(C_6H_9NO)_n$ generally can have molecular weights of 10,000-700,000. Hydrophilic organic fillers can be added including acrylic polymers, polyacrylic acid, polyvinyl alcohol, polyvinylpropylene, polyethylene glycol, sugars such as glucose and lactose, larger polysaccharides, and materials of cellulose origin. A benefit of combining the silicone adhesive with polyacrylic acid for example, is demonstrated by its ability to adhere more strongly, and for a longer period of time, to mucosal surfaces such as the internal mouth cavity. Hydrophobic release modulators can be added including glycerin, citrates, carbophil, and carbonates. The release modulators can also consist of sugar siloxanes such as described in U.S. Pat. No. 4,591,652 (May 27, 1986), U.S. Pat. No. 5,831,080 (Nov. 3, 1998), U.S. Pat. No. 6,517,933 (Feb. 11, 2003), WO 2003/50144 (Jun. 19, 2003), and WO 2004/24799 (Mar. 25, 2004). Other organic materials can be included such as stearyl alcohol, beeswax, lanolin, mineral oil, paraffin, petrolatum, and isopropyl myristate. These types of components can be used to alter one or more of the physical and drug delivery properties of the adhesive.

Preparation of the Silicone Adhesive

The silicone adhesive may be prepared by mixing the ingredients in any order. In particular, the silicone adhesive can be made by combining the several components in the amounts indicated below. These amounts are based on the total weight of the silicone adhesive composition unless otherwise specified.

(i) 13-25 percent by weight of the silicone resin;
(ii) 8-20 percent by weight of the linear organopolysiloxane fluid containing silicon-bonded hydroxy groups;
(iii) 5-30 percent by weight of the trialkylsiloxy terminated polyorganosiloxane fluid;
(iv) 5-25 percent by weight of the water soluble muco-adhesive polymer;
(v) 0-35 percent by weight of the solvent;
(vi) 0-10 percent by weight of the silicone polyether;
(vii) 0-15 percent by weight of the silicone wax;
(viii) 0-35 percent by weight of the drug, excipient, and/or active ingredient; and
(ix) 0-50 percent by weight of miscellaneous optional components.

Uses of the Silicone Adhesive

The silicone adhesive composition of the invention is useful for human, veterinary, and agricultural applications in general, and provides an adhesive material that adheres to wet surfaces, especially wet biological surfaces. These surfaces may include wet skin; the buccal cavity; the gums; the mucosal linings of other bodily canals and orifices including intranasal passages; the alimentary canal; and vaginal and rectal walls; as well as wet components of botanical origin including wood. The silicone adhesive composition can be used to act solely to attach a device such as a denture, a hairpiece, a prosthesis, an ostomy, a wound dressing, or a tape, to wet bodily surfaces; or it may function as a component in delivering an active ingredient such as pharmaceuticals, vitamins and/or other remedies of natural, synthetic, or botanical origin. The silicone adhesive composition can also be used to attach and/or participate in delivering an active ingredient or pharmaceutical, as in buccal and transdermal patches, or other dental, suppository, intranasal, aural, alimentary, or peritoneal delivery methods. The silicone adhesive compositions is capable of adhering to many other substrates such as paper, cloth, glass cloth, silicone rubber, polyethylene, polyethylene terephthalate, polytetrafluoroethylene, glass, wood, and metals.

Applying the Silicone Adhesive

When applying the silicone adhesive composition of the invention as a coating to a substrate, this can be carried out by (a) heating the silicone adhesive composition to a coatable temperature above 25° C., (b) coating the heated silicone adhesive composition onto the substrate, and (c) cooling the coated silicone adhesive composition until it is in a generally non-flowing state. Generally, heating the silicone adhesive composition to temperatures of about 100-150° C. results in suitable viscosities. These coating temperatures are low enough, so that decomposition of the silicone adhesive composition does not occur. Lower temperatures may result in coatable viscosities, depending on the coating equipment used, the desired end product, and the composition of the silicone adhesive. For example, the thicker the layer of silicone adhesive desired, the higher the coating viscosity can be. When the silicone adhesive compositions are applied to a backing or substrate, this may be accomplished using any conventional means such as roller coating, dip coating, extrusion, knife coating, or spray coating.

For example, in using the silicone adhesive composition, the composition containing an active ingredient such as a drug is applied to the backing substrate. A release liner is then placed over the silicone adhesive matrix containing the diffusible drug coated on the backing substrate. When a user desires to apply diffusible drug to a surface to be treated, the release liner is removed exposing the drug containing matrix, and the matrix containing the drug is placed on the surface. When the matrix is depleted of the drug, or after a predetermined period of time, the backing substrate and the depleted adhesive layer are removed from the treated surface. Liquid reservoirs containing the drug or active ingredient to be released can also be used rather than a solid matrix. When devices are to be applied to a surface, they can be permanently or releasably attached to the backing substrate. In some instances, the silicone adhesive composition can be coated directly on the device without a backing substrate. The device can be adhered to the surface by simply removing the release liner, and then placing the device on the surface.

Generally, the backing substrates are strips or patches of materials such as polymers, natural and synthetic wovens, non-wovens, foil, paper, and rubber. The backing substrate may be a single layer of material or a laminate of more than one layer. Generally, the backing substrate is substantially water impermeable. When the backing substrate is a polymer, it may comprise a single polymer or a mixtures of polymers.

Some examples of suitable polymers include polyethylene, ethylvinyl acetate, ethylvinyl alcohol, polyesters such as Mylar® manufactured by E.I. DuPont DeNemours and Company (DuPont), and fluoroplastics such as Teflon® manufactured by DuPont. Backing substrates are generally about one millimeter or less in thickness.

Release liners are typically rigid sheets of materials such as polyethylene, paper, and polyester. The release liners are generally coated with a non-stick type material such as a wax, silicone compounds, polyesters such as Teflon®, and other types of fluoropolymers. When the adhesive comprises a silicone adhesive composition, the release liner is preferably coated with a fluorosilicone or other fluoro-functional polymer. The release liners can be cut to substantially the same size and shape as the backing substrate, or they may be cut slightly larger than the backing substrate to provide a more readily accessible means for separating the release liners from the backing substrate.

EXAMPLES

The following examples are set forth in order to illustrate the invention in more detail. The adhesive composition used in the examples was an adhesive prepared via condensation of a linear organopolysiloxane fluid with silanol terminal functionality, and a silanol terminated silicone resin, generally as described in U.S. Pat. No. 2,857,356 (Oct. 21, 1958) noted above. The adhesive composition was a solid that was not easily manipulated in that form. The adhesive composition was therefore diluted in ethyl acetate to form a solution containing 60-65 percent by weight of the adhesive solids. The ethyl acetate was added to the adhesive solids to provide a viscosity that permitted the ready incorporation of other solid and liquid components into the adhesive composition. The silicone polyether used in the examples was a trimethylsiloxy terminated methyl(propyl)(polyethoxy)(hydroxy) polysiloxane having a viscosity of 335 $mm^2$/s at 25° C. In the examples, parts and percent are expressed in terms of parts by weight and percent by weight, respectively.

Example 1

The adhesive composition in this example was prepared by using 45 parts of the linear organopolysiloxane fluid and 55 parts of the silicone resin as described above, solvated in ethyl acetate as a solution containing 60 percent of the adhesive solids. To 17.6 gram of the 60 percent adhesive solution was added (i) 2.5 gram of a poly(ethylene oxide) polymer with an average molecular weight of 4,000,000, (ii) one gram of a methyl terminated polydimethylsiloxane having a viscosity of 60,000 $mm^2$/s at 25° C., (iii) 4.0 gram of a methyl terminated polydimethylsiloxane having a viscosity of 100 $mm^2$/s at 25° C., (iv) 1.25 gram of a silicone polyether, and (v) 6.91 gram of lidocaine. This composition was cast onto a Scotchpak 9956 release liner, and the solvent was allowed to evaporate to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 2

The adhesive composition in this example was prepared by using 50 parts of the linear organopolysiloxane fluid and 50 parts of the silicone resin as described above, solvated in ethyl acetate as a solution containing 60 percent of the adhesive solids. To 17.6 gram of the 60 percent adhesive solution was added (i) 2.5 gram of a poly(ethylene oxide) polymer with an average molecular weight of 4,000,000, (ii) one gram of a methyl terminated polydimethylsiloxane having a viscosity of 60,000 $mm^2$/s at 25° C., (iii) 4.0 gram of a methyl terminated polydimethylsiloxane having a viscosity of 100 $mm^2$/s at 25° C., (iv) 1.25 gram of a silicone polyether, and (v) 6.91 gram of lidocaine. This composition was cast onto a Scotchpak 9956 release liner, and the solvent was allowed to evaporate to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 3

The adhesive composition in this example was prepared by using 45 parts of the linear organopolysiloxane fluid and 55 parts of the silicone resin as described above, solvated in ethyl acetate as a solution containing 60 percent of the adhesive solids. To 17.6 gram of the 60 percent adhesive solution was added (i) 2.5 gram of a poly(ethylene oxide) polymer with an average molecular weight of 600,000, (ii) one gram of a methyl terminated polydimethylsiloxane having a viscosity of 60,000 $mm^2$/s at 25° C., (iii) 4.0 gram a methyl terminated polydimethylsiloxane having a viscosity of 100 $mm^2$/s at 25° C., (iv) 1.25 gram of a silicone polyether, and (v) 6.91 gram of lidocaine. This composition was cast onto a Scotchpak 9956 release liner, and the solvent was allowed to evaporate to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 4

The adhesive composition in this example was prepared by using 50 parts of the linear organopolysiloxane fluid and 50 parts of the silicone resin as described above, solvated in ethyl acetate as a solution containing 60 percent of the adhesive solids. To 17.6 gram of the 60 percent adhesive solution was added (i) 2.5 gram of a poly(ethylene oxide) polymer with an average molecular weight of 600,000, (ii) one gram of a methyl terminated polydimethylsiloxane having a viscosity of 60,000 $mm^2$/s at 25° C., (iii) 4.0 gram a methyl terminated polydimethylsiloxane having a viscosity of 100 $mm^2$/s at 25° C., (iv) 1.25 gram of a silicone polyether, and (v) 6.91 gram of lidocaine. This composition was cast onto a Scotchpak 9956 release liner, and the solvent was allowed to evaporate to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 5

The adhesive composition in this example was prepared by using 60 parts of the linear organopolysiloxane fluid and 40 parts of the silicone resin as described above, solvated in ethyl acetate as a solution containing 60 percent of the adhesive solids. To 55 gram of the 60 percent adhesive solution was added (i) 2.5 gram of a methyl terminated polydimethylsiloxane having a viscosity of 100 mm$^2$/s at 25° C. and (ii) 2.5 gram of a silicone polyether. A paste was prepared by combining (iii) 2 gram lidocaine and (iv) 2.5 gram of a methyl terminated polydimethylsiloxane fluid having a viscosity of 60,000 mm$^2$/s at 25° C., and then blending them together in a mortar and pestle. This paste was added to the solvated adhesive solution and mixed with a malt mixer. Five gram of (v) hydroxyethylcellulose was added to the mixture and mixed until a homogenous suspension was obtained. This composition was cast onto a fluoropolymer coated release liner, and the solvent was allowed to evaporate in a force draft oven at 120° C. to create a film.

The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 6

The adhesive composition in this example was prepared by using 60 parts of the linear organopolysiloxane fluid and 40 parts of the silicone resin as described above, solvated in ethyl acetate as a solution containing 60 percent of the adhesive solids. To 55 gram of the 60 percent adhesive solution was added (i) 5 gram of a methyl terminated polydimethylsiloxane having a viscosity of 100 mm$^2$/s at 25° C. and (ii) 2.5 gram of a silicone polyether. A paste was prepared by combining (iii) 2 gram lidocaine, and (iv) 2.5 gram methyl terminated polydimethylsiloxane fluid having a viscosity of 60,000 mm$^2$/s at 25° C., and then blending them together in a mortar and pestle. This paste was added to the solvated adhesive solution and mixed with a malt mixer. Five gram of (v) an acrylic acid based polymer was added to the mixture and mixed until a homogenous suspension was obtained. This composition was cast onto a fluoropolymer coated release liner, and the solvent was allowed to evaporate in a force draft oven at 120° C. to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Example 7

The adhesive composition in this example was prepared by using 60 parts of the linear organopolysiloxane fluid and 40 parts of the silicone resin as described above, solvated in ethyl acetate as a solution containing 60 percent of the adhesive solids. To 55 gram of the 60 percent adhesive solution was added (i) 2.5 gram of a methyl terminated polydimethylsiloxane having a viscosity of 100 mm$^2$/s at 25° C., and (ii) 2.5 gram of a silicone polyether. A paste was prepared by combining (iii) 2 gram of lidocaine and (iv) 2.5 gram of a methyl terminated polydimethylsiloxane fluid having a viscosity of 60,000 mm$^2$/s at 25° C., that were blended together in a mortar and pestle. This paste was added to the solvated adhesive solution and mixed with a malt mixer. Five gram of (v) polyvinylpyrrolidone was added to the mixture and mixed until a homogenous suspension was obtained. This composition was cast onto a fluoropolymer coated release liner, and the solvent was allowed to evaporate in a force draft oven at 120° C. to create a film. The film was applied to the skin of a human forearm while the forearm was submerged under a bath of tap water at a temperature of 25-30° C. The forearm was placed under the water for about one minute prior to applying the film. The forearm and the film were under water when the film was applied. It was observed that the film adhered to the skin of the forearm while the forearm was submerged, and that it remained on the forearm when the forearm was removed from the water bath.

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A method of adhering a device to a wet biological surface, which comprises
    applying to the device a silicone adhesive composition, wherein the silicone adhesive composition comprises:
        (i) 13 to 25 weight percent of a silicone resin that a cohydrolysis product of a trialkyl hydrolyzable silane and an alkyl silicate in which the cohydrolysis product contains a plurality of silicon-bonded hydroxy groups;
        (ii) 8 to 20 weight percent of a linear organopolysiloxane fluid containing terminal silicon-bonded hydroxy groups having a viscosity above 200,000 mm$^2$/s at 25° C.;
        (iii) 5 to 30 weight percent of a trialkylsiloxy terminated polyorganosiloxane fluid having a viscosity of 100,000-600,000 mm$^2$/s at 25° C.;
        (iv) 5 to 25 weight percent of a water soluble mucoadhesive polymer selected from the group consisting of a poly(ethylene oxide) polymer having a molecular weight of 100,000 to 8,000,000, an acrylic acid polymer having a molecular weight of 500,000 to 4,500,000,000, and a hydroxyethylcellulose polymer having a molecular weight of 90,000 to 1,300,000,000;
    and optionally,
        (v) up to 35 weight percent of a solvent selected from the group consisting of aliphatic hydrocarbons, aromatic hydrocarbons, esters, volatile linear and cyclic silicone compounds; and
    placing the device with the applied silicone adhesive composition to the wet biological surface, wherein the device is a denture, a hairpiece, a prosthesis, an ostomy, a wound dressing, a tape, a buccal patch, or a transdermal patch, and the wet surface is skin, the buccal cavity, the gums, the mucosal linings of intranasal passages, the alimentary canal, vaginal and rectal walls, and wet components of botanical origin.

2. A method according to claim 1 in which the silicone adhesive composition further comprises up to 10 weight percent of a silicone polyether.

3. A method according to claim 1 in which the silicone adhesive composition further comprises up to 15 weight percent of a silicone wax.

4. A method according to claim 1 in which the silicone adhesive composition further comprises up to 35 weight percent of a drug, an excipient and/or an active ingredient.

* * * * *